US00PP34284P2

(12) United States Plant Patent
Hansen

(10) Patent No.: US PP34,284 P2
(45) Date of Patent: May 31, 2022

(54) ***HOSTA* PLANT NAMED 'SEASONS IN THE SUN'**

(50) Latin Name: ***Hosta* hybrid (Tratt.)**
Varietal Denomination: Seasons in the Sun

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 17/300,988

(22) Filed: Jan. 10, 2022

(51) Int. Cl.
*A01H 5/02* (2018.01)
*A01H 6/12* (2018.01)

(52) U.S. Cl.
USPC ..... Plt./353
CPC ..... *A01H 6/12* (2018.05)

(58) Field of Classification Search
USPC ..... Plt./353
CPC ..... A01H 5/02; A01H 5/12
See application file for complete search history.

*Primary Examiner* — Kent L Bell

(57) ABSTRACT

A new and distinct *Hosta* plant named 'Seasons in the Sun' producing medium-sized rounded mounds of basal, cordate to nearly rounded, leaves with mucronulate apices, cordate bases and slightly wavy margins. The leaves are chartreuse beginning in spring and become a light yellow with sufficient sunlight as the season progresses. The campanulate flowers are near white with light lavender center stripes and are held just above the foliage beginning in early July. 'Seasons in the Sun' is useful in the landscape, as a container plant, a specimen or en masse.

2 Drawing Sheets

Botanical classification: *Hosta* hybrid (Tratt.).
Variety denomination: 'Seasons in the Sun'.

STATEMENT REGARDING PRIOR DISCLOSURES UNDER 37 CFR 1.77(b)(6)

*Hosta* 'Seasons in the Sun' was first introduced by the inventor as a non-enabling description in registration of the name in early 2021 with the International Cultivar Registration Authority for the genus *Hosta*. No plants of *Hosta* 'Seasons in the Sun' have been sold in this country or anywhere in the world, nor has any enabling disclosure of the new plant been made.

BACKGROUND AND ORIGIN OF THE PLANT

The present invention relates to a new and distinct *Hosta* plant, *Hosta* 'Seasons in the Sun' hereinafter also referred to as the new plant or by the cultivar name, 'Seasons in the Sun'. *Hosta* 'Seasons in the Sun' was hybridized by the inventor on Jul. 14, 2014 at a wholesale perennial nursery in Zeeland, Mich., USA. The female parent was the proprietary, unnamed unreleased hybrid known only as H10-394-1 (not patented) and the male parent was the proprietary, unnamed unreleased hybrid known only as H11-304-1 (not patented). The seeds from this cross were collected and planted in the spring of 2015 and a single seedling selection from this cross eventually produced the new plant. The new plant was assigned the breeder code 14-324-1 and passed the initial evaluation in the summer of 2018. 'Seasons in the Sun' has been asexually propagated by division at the same nursery since 2018 and also by careful shoot tip plant tissue culture with the resultant asexually propagated plants having retained all the same traits as the original plant. *Hosta*

'Seasons in the Sun' has been stable and reproduced true to type plants in successive generations of asexual reproduction.

There are nearly 7,000 registered and established *Hosta* cultivars with The American *Hosta* Society, which is the International Cultivar Registration Authority for the genus *Hosta*. Several of these have blue-green leaf blades. The most similar *Hosta* cultivars known to the applicant are: 'Solar Flare' U.S. Plant Pat. No. 7,046, 'Glory' (not patented), 'Coast to Coast' U.S. Plant Pat. No. 26,469, 'Sun Mouse' U.S. Plant Pat. No. 30,033, 'Age of Gold' U.S. Plant Pat. No. 30,902, 'Abiqua Recluse' (not patented) and 'Key West' (not patented).

The female parent is larger and more mounded and less upright in habit with larger, smoother, and with yellow foliage. The male parent has a less upright habit with more wedge-shaped yellow-colored and flat foliage.

The habit of 'Solar Flare' is larger and more arching in habit with leaves more chartreuse, larger and longer. 'Glory' has a smaller habit with smaller foliage and the flowers are more capitate, flower scape with deeper lavender flowers. 'Coast to Coast' has a larger habit with leaves that are larger, more ovate, more bullate with a more mucronate apex, and the flowers are more lavender. 'Sun Mouse' is a much smaller plant with smaller foliage and flowers of light purple on more erect scapes. 'Age of Gold' has a shorter more rounded leaf without the sinuate margin or bullate surface. 'Abiqua Recluse' has foliage that is more bullate and the flower scapes are more upright with smaller floral bracts that are more green. 'Key West' has a larger more horizontal habit with more erect and taller scapes and larger more ovate foliage that is less bullate and more chartreuse and less yellowish.

Other *Hosta* cultivars may have individual traits similar to 'Seasons in the Sun', but the new plant differs from the above listed cultivars and all other *Hostas* known to the applicant, by the combination of the following traits.

1. Leaves are medium-sized, cordate to nearly rounded, with mucronulate apices and cordate bases;
2. Leaves have a slightly wavy margin, bullate surface between the veins, and slightly impressed adaxial veins with a mucronulate apex;
3. Leaf color emerges chartreuse becoming lutescent as the season progresses;
4. Campanulate flowers are near white with pale lavender centers on angular outwardly, yellow-green-colored scapes beginning in early-July;
5. Flowers are densely arranged on scapes with the first flowers beginning to open just above the foliage;
6. The habit is a medium-sized rounded mound.

BRIEF DESCRIPTION OF THE DRAWING

The photographs of the new plant demonstrate the overall appearance of the new plant, including the unique traits. The colors are as accurate as reasonably possible with color reproductions. Ambient light spectrum, temperature, source and direction may cause the appearance of minor variation in color.

The drawings show a six-year-old plant of 'Seasons in the Sun' in a shaded trial garden at a nursery in Zeeland, Mich. with supplement fertilizer and water as needed.

DETAILED BOTANICAL DESCRIPTION

Figure 1:
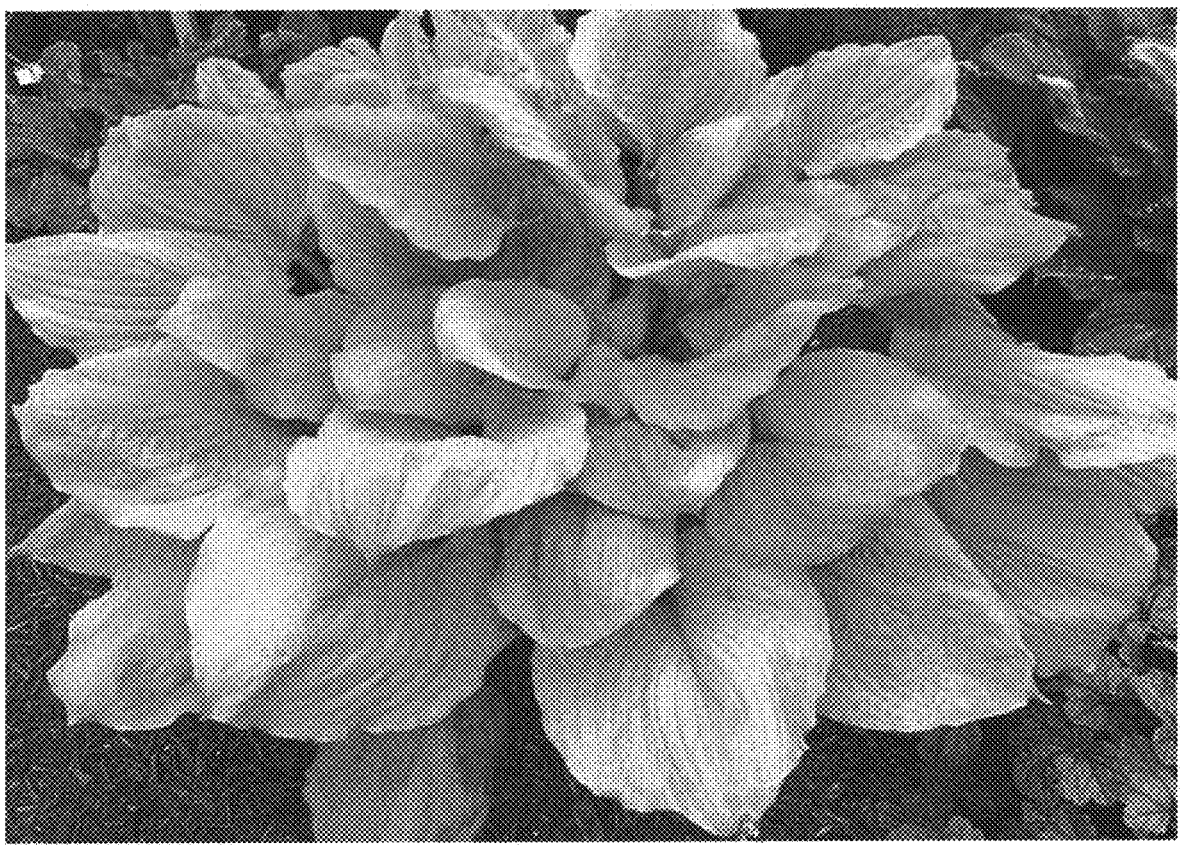
FIG. 1 shows the landscape foliage habit of a plant in late summer.
Figure 2:
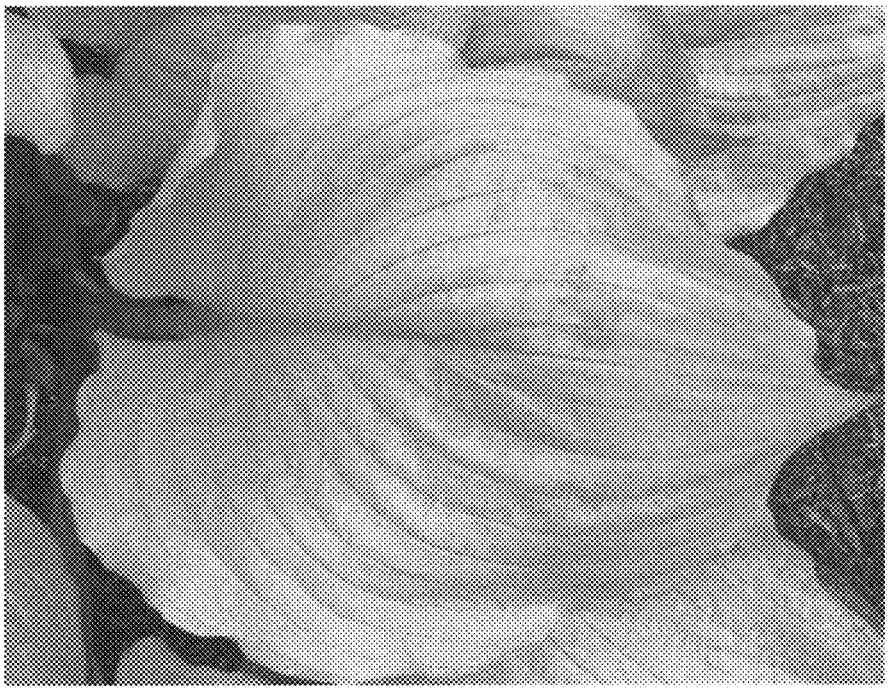
FIG. 2 shows a close-up of a leaf of a plant.
Figure 3:
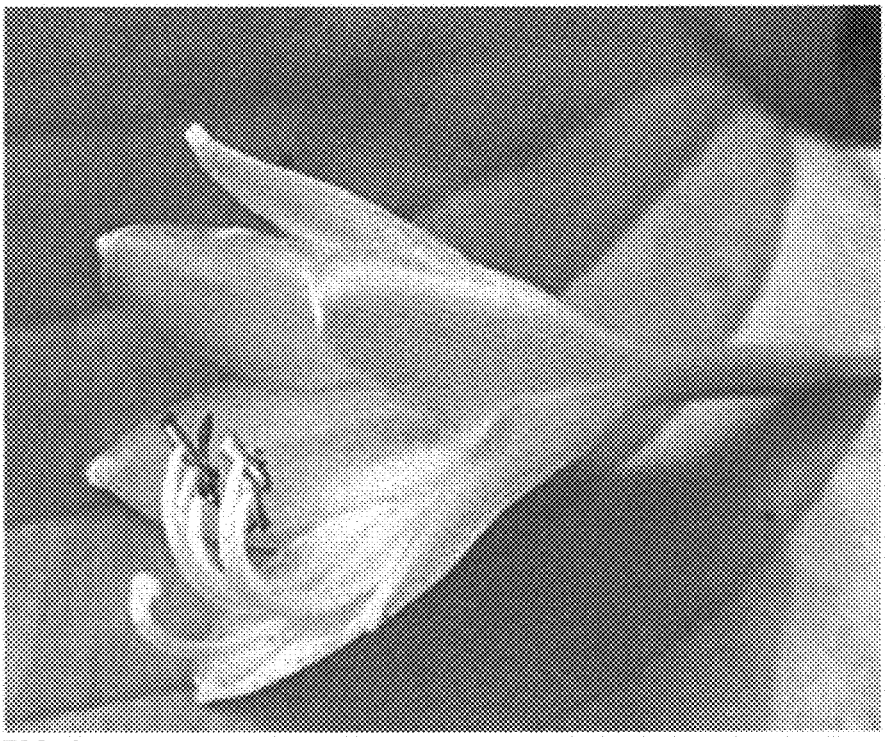
FIG. 3 shows a close-up of the flower on a leaf.

The following descriptions and color references are based on the 2015 edition of The Royal Horticultural Society Colour Chart except where common dictionary terms are used. The new plant, *Hosta* 'Seasons in the Sun', has not been observed under all possible environments. Those skilled in the art will appreciate that certain characteristics will vary with plants that are more mature or plants that are less mature. The phenotype may vary slightly with different environmental conditions, such as temperature, light, fertility, moisture and maturity levels, but without any change in the genotype. The following observations and size descriptions are of a six-year-old plant in a shaded trial garden in Zeeland, Mich. with supplemental water and fertilizer.

Botanical classification: *Hosta* x hybrid;

Parentage: Female or seed parent is a proprietary hybrid H10-394-1; male or pollen parent is the proprietary hybrid H11-304-1;

Propagation: Garden division and sterile shoot tip tissue culture;

Time to initiate roots from tissue culture: About three weeks;

Growth rate: Moderately vigorous;

Crop time: About three months to five months to finish during the spring in a one-liter container from rooted tissue culture plantlet during the warm portion of the growing season;

Rooting habit: Fleshy, lightly branching;

Root color: Nearest RHS NN155C when actively growing;

Plant shape and habit: Hardy herbaceous perennial with basal rosette of leaves emerging from rhizomes producing a medium-sized mound of outwardly to slightly upwardly petioles and leaves and mostly outwardly angled scapes flowering slightly above the foliage;

Plant size: Foliage height to about 70 cm above soil line to the top of the leaves, to about 100 cm tall to the top of the flowers and to about 125 cm wide at the widest point just above the soil line;

Foliage description: Cordate to nearly rounded; mucronulate apex, cordate base; margin entire, and slightly sinuate; not folded, flat to slightly convex toward apex; surface slightly bullate between the veins; glabrous and slightly lustrous both surfaces; flexible; variegated;

Leaf blade size: To about 28 cm long and about 23 cm wide about halfway from the apex; average about 26 cm long and 21.5 cm wide;

Leaf blade color: Early season and expanding adaxial between RHS 144A and RHS N144A, abaxial between RHS 144A and RHS N144A; mid-season and mature adaxial variable, nearest RHS 11B, RHS 145A and between RHS 144A and RHS N144A, abaxial variable, nearest RHS 11B and between RHS 145B and RHS 11B;

Veins: 12 to 15 pairs with midrib; slightly impressed adaxial and costate and smooth abaxial;

Vein color: Young adaxial nearest RHS 145D and abaxial nearest RHS 145C; mature adaxial nearest RHS 145C and abaxial nearest RHS 147D;

Petiole: Glabrous and matte both adaxial and abaxial; moderately concavo-convex proximally and shallowly distally; stiff; outwardly; to 39 cm long and 12 mm wide at base and about 7 mm deep at base and 22 mm wide below leaf blade, average about 35 cm long and 11.0 mm wide and 6.0 mm deep;

Petiole color: Adaxial between RHS 144B and RHS 145A, abaxial midrib nearest RHS 145C and region surrounding midrib between RHS 145C and RHS 147D;

Flower description:

Buds one to two days prior to opening: Clavate with acute apex and narrow tube and rounded base; about 44 mm long and 12 mm in diameter at the widest portion in the bulb, tube to about 18 mm long and to about 3 mm diameter at base, tapering rapidly beyond bulb;

Bud color: Between RHS NN155D and RHS 84D at bulb, and corolla tube nearest RHS 84D;

Flowers: Perfect; incomplete; campanulate; attitude slightly drooping; to 56.0 mm long to exserted pistil; corolla to 52 mm long and 30 mm wide at apex, fused in basal 32 mm, free in the distal 20 mm, decreasing in size distally; corolla tube portion 19 mm long and gradually tapering to 3 mm diameter at base; with rounded base; flowers tightly arranged on scape;

Flowering lasting: Persists for a normal period, usually individually about one day on plant;

Flowering period: Scapes remain effective with flowers beginning early July for about three weeks; with about 33 flowers per scape; mostly secund;

Fragrance: No detectable fragrance;

Tepal: Two sets of three; clavate; entire margins; acute apex; fused in basal 32 mm; glabrous adaxial and abaxial; outer set to about 9 mm wide and 54 mm long; inner set to about 9 mm wide and 54 mm long;

Tepal color: Outer set adaxial between RHS NN155D and RHS 85D in 3 mm longitudinal center and nearest RHS NN155D along edges, abaxial between RHS NN155D and lighter than RHS 85D; inner set adaxial nearest RHS 85D in 4 mm longitudinal center and nearest RHS NN155D along edges, abaxial between RHS NN155D and lighter than RHS 85D, without a transparent wide margin; corolla tube adaxial nearest RHS NN155C, abaxial between RHS NN155D and RHS 85D;

Gynoecium: Single; to about 56 mm long; superior;

*Style*.—Cylindrical; glabrous; to about 50 mm long and 0.7 mm diameter; straight with distal 6 mm arcuate upwards about 90°; color nearest RHS 145D proximally and RHS 155D distally.

*Stigma*.—Puberulent; globose; about 1 mm long and 1 mm diameter; color nearest RHS NN155A.

*Ovary*.—Ellipsoidal; superior; apex rounded; base rounded to truncate; sides slightly furrowed, about 5 mm long and 2.5 mm diameter; color nearest RHS 145A.

Androecium: Six;

*Filaments*.—Six; cylindrical; approximately 54 mm long and 0.5 mm in diameter; curved or bent upwardly about 90° in the distal 10 mm; color in distal one-half nearest RHS NN155C transitioning to nearest RHS 145D in the proximal one-third.

*Anthers*.—Oblong with rounded apices; basifixed, longitudinally dehiscent; about 5 mm long and 2 mm wide when fully developed; color nearest RHS 199B.

*Pollen*.—Abundant; spherical; less than 0.1 mm long; color nearest RHS 12A.

Peduncle: Cylindrical; usually one per mature division; about six per plant; glabrous; moderately glaucous; angular to arching; to about 99 cm long, and about 7 mm in diameter at base, average about 84 cm tall and 6.0 mm diameter at base;

Inflorescence: Flowering portion about 15 cm long and 7 cm wide; with single bract subtending each flower;

Peduncle color: Nearest RHS 146A;

Pedicel: Cylindrical; glabrous; slightly glaucous; to about 10 mm long and 2 mm diameter, decreasing distally; attitude outwardly in flower to arcuate downwardly with fruit;

Pedicel color: Nearest RHS 148D;

Floral bracts: Each flower normally subtended by a single bract; lanceolate; narrowly acute apex and truncate base; entire margin; glabrous and slightly lustrous abaxial and adaxial; to about 18 mm long 7 mm wide, decreasing distally; with one bract before flowers to about 3 cm long and 1 cm wide at base;

Bract color: At flowering adaxial and abaxial between RHS 76D and RHS 157C;

Fruit: Non-fleshy, dehiscent, tri-loculicidal capsule; oblong; rounded base; acute to apiculate apex; about 32 mm long and 6 mm in diameter; color as maturing nearest RHS 146B, when nearly mature and prior to dehiscence nearest RHS 150D and upon dehiscence nearest RHS 161C;

Seeds: Elliptic; with flattened wing surrounding embryo positioned toward one end of ellipse; about 6 mm long, 2.5 mm wide and 1 mm thick at embryo; typically 10 to 36 per capsule; color nearest RHS 202A with maturity;

Disease resistance: The thick glaucous leaves provide some resistance to slug feeding. Other resistance to pests (including: *Odocoileus virginianus* and *Oryctotagus cuniculus*) and diseases common to *Hostas* is equal that typical of other cultivars.

Growth: The new plant grows best and shows best coloration with plenty of moisture, adequate drainage and light shade, but is able to tolerate some drought when mature.

Hardiness: At least from USDA zone 3 through 8, and other disease resistance is typical of that of other *Hostas*.

It is claimed:

1. A new and distinct *Hosta* plant named *Hosta* 'Seasons in the Sun' as herein described and illustrated.

* * * * *